(12) United States Patent
Liu et al.

(10) Patent No.: US 9,120,917 B2
(45) Date of Patent: Sep. 1, 2015

(54) N-SUBSTITUTED ACRYLAMIDES, PREPARATION METHOD AND USE THEREOF

(75) Inventors: Zhaoqing Liu, Shanghai (CN); Floryan De Campo, Shanghai (CN)

(73) Assignee: SOLVAY CHINA CO., LTD., Shanghai (CN)

( * ) Notice: Subject to any disclaimer, the term of this patent is extended or adjusted under 35 U.S.C. 154(b) by 321 days.

(21) Appl. No.: 13/502,853

(22) PCT Filed: Oct. 30, 2009

(86) PCT No.: PCT/CN2009/074727
§ 371 (c)(1),
(2), (4) Date: Apr. 19, 2012

(87) PCT Pub. No.: WO2011/050534
PCT Pub. Date: May 5, 2011

(65) Prior Publication Data
US 2012/0202958 A1    Aug. 9, 2012

(51) Int. Cl.
C07F 9/00 (2006.01)
C08K 5/5353 (2006.01)
C07F 9/38 (2006.01)

(52) U.S. Cl.
CPC ............. C08K 5/5353 (2013.01); C07F 9/3826 (2013.01)

(58) Field of Classification Search
CPC .......................... C07F 9/3826; C08K 5/5353
See application file for complete search history.

(56) References Cited

U.S. PATENT DOCUMENTS

| 3,506,707 A | 4/1970 | Miller, at al. |
| 4,239,885 A | 12/1980 | Richmond |
| 4,526,728 A | 7/1985 | Finke et al. |
| 5,712,413 A | 1/1998 | Burrington et al. |
| 6,902,608 B2 | 6/2005 | Erdmann et al. |

FOREIGN PATENT DOCUMENTS

| CN | 101218267 | 7/2008 |
| DE | 3644009 | 6/1988 |
| EP | 0275470 | 7/1988 |
| GB | 2103216 | 2/1983 |
| JP | 2004-501940 | 1/2004 |
| JP | 2009-500481 | 1/2009 |

*Primary Examiner* — Clinton Brooks
(74) *Attorney, Agent, or Firm* — Xuping Fu

(57) ABSTRACT

This invention relates to new monomers prepared from phosphorus-containing diene monomers and (meth)acrylonitrile via Ritter reactions, and the preparation method thereof. The polymer of these monomers can be utilized in various applications such as water treatment, rheology modifier, surface modification, etc. The monomers have the following structure (II), Wherein $R_1$, $R_2$, $R_3$, $R_4$, $R_5$, $R_6$ and $R_7$ represent, independently, hydrogen, alkyl, aryl, alkaryl, aralkyl, cycloalkyl, heterocycloalkyl, or alkenyl groups; $R_6$ and $R_7$ represents $R_9O$, and $R_{10}$ respectively wherein $R_9$ and $R_{10}$ represents hydrogen, alkyl, aryl, alkaryl, aralkyl, cycloalkyl, alkenyl groups, or metals selected from the group consisting of Na, Li, Ca; $R_8$ represents H, or $CH_3$.

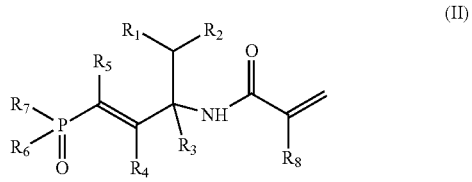

(II)

27 Claims, No Drawings

N-SUBSTITUTED ACRYLAMIDES, PREPARATION METHOD AND USE THEREOF

CROSS REFERENCE TO RELATED APPLICATIONS

This application claims priority to international application no. PCT/CN2009/074727, filed Oct. 30, 2009. The contents of the aforementioned application are incorporated herein in their entirety.

TECHNICAL FIELD

This invention relates to N-substituted acrylamides bearing phosphonic acid and/or other relevant phosphorus functional groups, the preparation method and use thereof.

BACKGROUND

Functionalized (meth)acrylamides are important class of specialty monomers. These types of monomers are considered the most reactive ones and their polymers and co-polymers have been used in both industrial and consumer products such as water-treatment, coating, oil fields, home and personal care products. Most of the functionalized (meth)acrylamides are produced by Ritter reactions from readily available acrylonitrile (for Ritter reactions: Organic Process Research & Development 1999, 3, 232234 & K. L. Reddy Tetrahedron Letters 44 (2003) 1454 1453-1455).

U.S. Pat. No. 3,506,707 described acrylamidoalkanesulfonic acids prepared by a two step reaction sequence comprising first reacting an olefinic compound containing at least one allylic hydrogen atom with an acyl hydrogen sulfate to form a sulfonated intermediate, and subsequently reacting this intermediate with an acrylonitrile in the presence of sulfuric acid and then with water. U.S. Pat. No. 4,239,885 described a process for the preparation of diacetone acrylamide whereby acrylonitrile and diacetone alcohol are reacted in at least 93% sulfuric acid to form a novel intermediate reaction product which is recovered as a crystalline solid, washed with an organic solvent to remove colored oily impurities along with sulfuric acid, and hydrolyzed to produce diacetone acrylamide. U.S. Pat. No. 5,712,413 described a process for the preparation of N-hydrocarbyl-substituted amides such as tert-butylacrylamide via the Ritter reaction using solid heteropolyacid catalysts. DE 86-3644009 (1988) described N-Substituted acrylamides containing ester groups. GB 2103216 described a process for preparing N-alkylamides of acrylic acid or methacrylic acid, wherein acrylonitrile or methacrylonitrile is reacted with a compound having an optionally substituted alkyl group with 3 to 40 carbon atoms, capable of forming an alkyl carbonium ion under the effect of sulphuric acid.

There is a market need for reactive monomers bearing phosphonic acid and other relevant phosphorus functional groups. The polymer from these monomers will find various applications such as water treatment, rheology modifier, surface modification, etc.

U.S. Pat. No. 4,526,728 described a way to make 2-(meth)acrylamido-2-methylpropanephosphonic acid from isobutene, $PCl_5$ and (meth)acrylonitrile. However, the yields were low and large amounts of hazardous wastes were generated from the process. There still are needs for reactive (meth)acrylamide monomers bearing phosphonate or phosphinate functional groups with an efficient process.

SUMMARY OF THE INVENTION

In general, this invention relates to new monomers of N-substituted acrylamides of the formula II prepared from phosphorus-containing diene monomers and (meth)acrylonitrile via Ritter reactions.

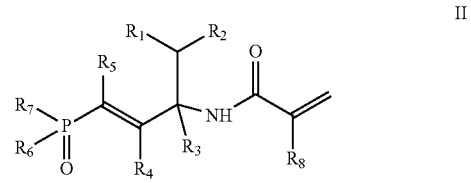

Also, this invention relates to the preparation method of said monomers.

The polymer from these monomers will find various applications such as water treatment, rheology modifier, surface modification, etc. Further derivatization of the monomer will also generate phosphonic or phosphinic acid-containing surfactants etc.

DETAILED DESCRIPTION OF THE INVENTION

In one aspect, the present invention provides the following compounds of formula II,

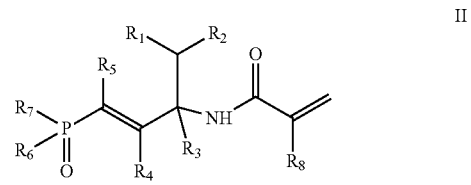

Wherein, $R_1$, $R_2$, $R_3$, $R_4$, $R_5$, $R_6$ and $R_7$ represent, independently, hydrogen, alkyl, aryl, alkaryl, aralkyl, cycloalkyl, heterocycloalkyl, or alkenyl groups; preferably, the said alkyl, alkenyl comprise from 1~24 carbon atoms, said aryl comprises from 6~24 carbon atoms, said alkaryl, aralkyl comprise from 7~24 carbon atoms, and said cycloalkyl, heterocycloalkyl comprise from 3~24 carbon atoms; more preferably, the said alkyl, alkenyl comprise from 1~18 carbon atoms, said aryl comprises from 6~18 carbon atoms, said alkaryl, aralkyl comprise from 7~18 carbon atoms, and said cycloalkyl, heterocycloalkyl comprise from 3~18 carbon atoms; more preferably, $R_1$, $R_2$, and $R_4$ represent hydrogen; or $R_3$ and $R_5$ represent methyl.

Preferably, $R_1$ and/or $R_2$ represent hydrogen, so the monomers so obtained are more reactive toward polymerization.

$R_6$ and $R_7$ represents $R_9O$, and $R_{10}O$ wherein $R_9$ and $R_{10}$ represents hydrogen, alkyl, aryl, alkaryl, aralkyl, cycloalkyl, alkenyl groups, or metals selected from the group consisting of Na, Li, Ca. Preferably, $R_6$ and $R_7$ represent $R_9O$ and $R_{10}O$, respectively, $R_9=R_{10}=H$. Preferably, the said alkyl, alkenyl comprise from 1~24 carbon atoms, said aryl comprises from 6~24 carbon atoms, said alkaryl, aralkyl comprise from 7~24 carbon atoms, and said cycloalkyl, heterocycloalkyl comprise from 3~24 carbon atoms; more preferably, the said alkyl, alkenyl comprise from 1~18 carbon atoms, said aryl comprises from 6~18 carbon atoms, said alkaryl, aralkyl comprise from 7~18 carbon atoms, and said cycloalkyl, heterocycloalkyl comprise from 3~18 carbon atoms;

Most preferably, $R_1$, $R_2$, and $R_4$ represent hydrogen, $R_3$, $R_5$ represent methyl and wherein $R_6$ and $R_7$ represent $R_9O$ and $R_{10}O$, $R_9=R_{10}=H$.

$R_8$ represents H, or $CH_3$.

Those skilled in this technical field should understand that, the terms of '$R_xO$' refer to substituents having the structures of '$R_x$—O—'. For example, '$R_9O$' refers to a substituent having the structure of '$R_9$—O—'.

In one of the preferred embodiments of the present invention, any two of $R_1$, $R_2$, $R_3$, $R_4$, $R_5$, $R_6$ and $R_7$ are together formed into a cycloalkyl, or heterocycloalkyl group, which is preferably selected from 3~8 membered rings.

In another one of the preferred embodiments of the present invention, any two of $R_1$, $R_2$, $R_3$, $R_4$, $R_5$, $R_9$ and $R_{10}$ are together formed into a cycloalkyl, or heterocycloalkyl group, which is preferably selected from 3~8 membered rings.

Unless otherwise defined herein or below in the remainder of the specification, "Compounds of the present invention" or "compounds prepared according to the present invention" refers to compounds encompassed by the various description and structural formula disclosed herein. The compounds may be identified by either their chemical structure and/or chemical name.

The compounds of the present invention may contain one or more chiral centers and/or double bonds and therefore may exist as stereoisomers, such as Z- and E- or cis- and trans-isomers from cyclic structures or double bonds (i.e., geometric isomers), rotamers, enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures, with the exception that when only one enantiomer is specified, the structure inclues the other enantiomer as well. For example, in the event that a compound of formula II disclosed in the present invention is Z-form or trans-form for the double bonds close to P, one skilled in this art should understand that the E-form or cis-form of the compound is also disclosed. Enantiomeric and stereoisomeric mixtures can be resolved into their component enantiomers or stereoisomers using separation techniques or chiral synthesis techniques well known to those skilled in this art.

In one other aspect, the present invention provides a method for preparing a compound of formula II, which comprises the step of reacting a compound of formula I with (meth)acrylonitrile. According to the present invention, compounds of formula II can be prepared from phosphorus-containing diene monomers and (meth)acrylonitrile via Ritter reactions.

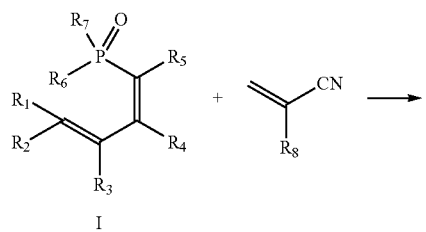

I

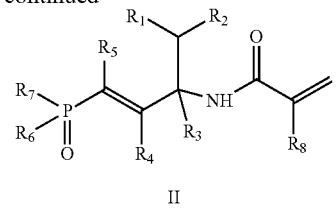

II

Wherein, all the substituents of $R_1$~$R_8$ refer to the preceding definitions of $R_1$~$R_8$.

Preferably, according to the method of the present invention, said compound I is added in the molar ratio of (0.1~1):1 relative to said (meth)acrylonitrile, or preferably (0.8~1):1 relative to said (meth)acrylonitrile. The reaction time remains 4~24 hours, or preferably 5~18 hours. The reaction temperature remains 0~100° C., or preferably 30-60° C.

The diene monomers of formula I can be prepared from α,β- or β,γ-unsaturated ketones and aldehydes.

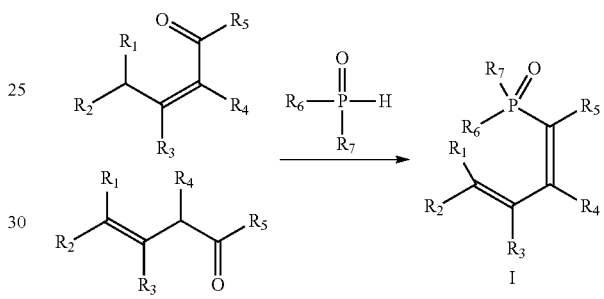

I

For example, mesityl oxide was reacted with phosphorous acid in the presence of acetic anhydride and acetic acid under mild conditions to yield 4-methylpenta-2,4-diene-2-phosphonic acid in more than 90% purity.

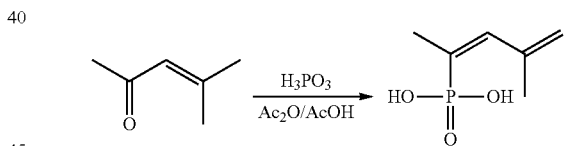

In one other aspect, the present invention provides the use of compounds of formula II according to the present invention, or of polymers or co-polymers of compounds of formula II according to the present invention. For example, but not to limit this invention, the compounds of formula II according to the present invention can be utilized as monomers to prepare polymers or co-polymers. The compounds of the present invention, or the polymers or co-polymers can be used in various applications such as water treatment applications, rheology modifier applications, surface treatment applications, oilfield applications, mining applications, dental applications, plastics, and etc. . . . preferably, the compounds of the present invention or their polymers or co-polymers can be used as flame retardants in plastics or textile. The invention also relates to a method for preparing polymers or co-polymers of compounds of formula II, comprising a step of preparing a compound of formula II according to the method of the present invention and a polymerization or co-polymerization step. The present invention also provides polymers or co-polymers of compounds of formula II according to the present invention.

Further derivatization of the monomer will also generate phosphonic acid-containing surfactants etc.

The invention is further described by the examples below.

EXAMPLES OF THE PRESENT INVENTION

The following examples are offered to illustrate, but not to limit the present invention.

Example 1

Phosphorous acid, $H_3PO_3$ 200 g, which was dried for about 4 hrs at 50° C. under vacuum, and 194 g of acetic acid were added to a 2 L flask with cooling. Then 494 g of acetic anhydride was charged and the temperature rose to 25° C. to yield a colorless homogenous mixture. 1 g of phenothiazine was added and the reaction mixture became light orange. Mesityl oxide (a mixture of 1.2 and 1.3 isomers) 284 g was added drop-wise with stirring over about 4 hrs and the temperature was kept at 23~25° C. The color of the reaction mixture became dark orange after the unsaturated ketone addition. The mixture was then heated to 48° C. for 7 hrs. The reaction was monitored by $^{31}P$ NMR ($D_2O$) in term of % mole as shown in the following table:

| Rx time, h | Peak, δ | | | |
| --- | --- | --- | --- | --- |
| | The unknown, 39~32 ppm | Product, 20 ppm | Anhydrides of the Product, 11 ppm | $H_3PO_3$ 4 ppm |
| 0 | 8.34 | 35.65 | 11.6 | 44.05 |
| 1 | 8.12 | 37.05 | 13.52 | 39.37 |
| 2 | 10.33 | 47.70 | 19.02 | 22.12 |
| 3 | 11.52 | 46.82 | 22.82 | 16.92 |
| 4 | 11.95 | 43.77 | 24.07 | 15.67 |
| 7 | 9.47 | 37.25 | 56.70 | 0 |

The product, 4-methyl-2,4-pentadiene-2-phosphonic acid (PoDM) and its anhydride derivative were observed in more than 90% yield with 100% conversion of phosphorous acid.

Example 2

The reaction mixture from Example 1, 620 g, was added 75 ml of water. The resulting solution was heated at 50° C. for 5 hrs until no product derivative was observed as monitored by $^{31}P$ NMR in $D_2O$, and then acetic acid was removed under vacuum of 5 mPa at 50° C. for 6 hrs until no solvent came out to yield 250 g of brown oil. $^{31}P$ NMR showed 87.4% mole was PoDM, while HPLC analysis showed 96.1% area at UV of 214 nm and 87.3% area at UV of 254 nm for PoDM. HPLC-MS analysis showed the molecular weight of the product to be 162.1 and both C-13 and H-1 NMR confirmed the structure of PoDM. $^1H$ NMR ($D_2O$, ppm): δ6.30 (d, 1H), 4.95 (s, 1H), 4.79 (s, 1H), 1.78 (d, 3H) and 1.75 (s, 3H). $^{13}C$ ($D_2O$, ppm), δ141.6 (d), 141.1 (d), 126.7 (d), 21.8 (s), 13.4 (d).

Example 3

25 g (0.129 mole) of PoDM from Example 2, 0.02 g of phenothiazine and 10.3 ml (0.156 mole) of acrylonitrile were added to a flask cooled with cold water. Then 7 ml of $H_2SO_4$ was added slowly with mixing while the batch was cooled at 30° C. The mixture became homogenous thick oil after the addition and it was stirred at 30° C. for 4 hrs and then at 60° C. for 1 hr. After the reaction was done, acrylonitrile was removed under vacuum. 100 ml of water was poured into the mixture and 7 g (0.129 mol) of calcium oxide was added slowly with stirring. After 2 hours mixing, the precipitation was suction filtrated, washed with a small amount of water. The obtained aqueous solution was concentrated in vacuum at 40° C. for 3 hrs to yield brown oily product. HPLC analysis showed 4-acrylamido-4-methyl-2-pentene-2-phosphonic acid (AMPP) to be 93.2% by area integration at UV 214 nm while $^{31}P$ NMR showed 78.3% by mole of AMPP along with other two unknown phosphorus-containing impurities. A white solid product was obtained with acetone precipitation. The product was found to be hygroscopic and it turned to be liquid upon exposure to air. LC-MS (ES-API) showed molecular ion at 234.1 together with its dimeric at 467.1 and trimeric at 700.2. $^{31}P$ ($D_2O$), 19.8 ppm. $^1H$ NMR ($D_2O$, δ ppm): δ5.90 (d, 1H), 5.74 (m, 1H), 5.59 (d, 1H), 5.18 (d, 1H), 1.27 (d, 3H) and 0.91 (s, 6H). $^{13}C$ NMR ($D_2O$, δ ppm), δ166.4, 146.9, 129.5, 127.3 & 126.1 (d), 124, 26.6 and 11.6 (d).

Example 4

10 g (0.121 mole) of vacuum dried $H_3PO_3$, 14.2 g (0.145 mole) of mesityl oxide, 9.7 g of acetic acid, 0.01 g of phenothiazine and 10.3 ml (0.156 mole) of acrylonitrile were mixed in a flask at 28° C. Then 24.7 g of acetic anhydride was added slowly over about 70 min. while the temperature was kept below 30° C. After the addition, the mixture was heated to 48° C. over night at 48° C. and then at 60° C. for another 2 hours. $^{31}P$ NMR showed 95% $H_3PO_3$ was converted with 86% selectivity to AMPP and the majority of its precursor PoDM. Further conversion of PoDM to AMPP could be done if sulfuric acid was used after the reaction.

What is claimed is:
1. Compounds of formula II,

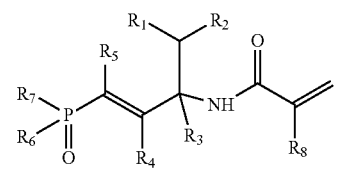

Wherein,
$R_1$, $R_2$, $R_3$, $R_4$, $R_5$, $R_6$ and $R_7$ represent, independently, hydrogen, alkyl, aryl, alkaryl, aralkyl, cycloalkyl, heterocycloalkyl, or alkenyl groups;
$R_6$ and $R_7$ represents $R_9O$, and $R_{10}O$ respectively wherein $R_9$ and $R_{10}$ represents hydrogen, alkyl, aryl, alkaryl, aralkyl, cycloalkyl, alkenyl groups, or metals selected from the group consisting of Na, Li, Ca;
$R_8$ represents H, or $CH_3$; and
wherein any two of $R_1$, $R_2$, $R_3$, $R_4$ and $R_5$ are together formed into a cycloalkyl, or heterocycloalkyl group.
2. The compounds of claim 1, wherein the said alkyl, alkenyl comprise from 1~24 carbon atoms, said aryl comprises from 6~24 carbon atoms, said alkaryl, aralkyl comprise from 7~24 carbon atoms, and said cycloalkyl, heterocycloalkyl comprise from 3~24 carbon atoms.
3. The compounds of claim 1, wherein the said alkyl, alkenyl comprise from 1~18 carbon atoms, said aryl comprises from 6~18 carbon atoms, said alkaryl, aralkyl comprise from 7~18 carbon atoms, and said cycloalkyl, heterocycloalkyl comprise from 3~18 carbon atoms.
4. The compounds of claim 1, wherein $R_1$ and/or $R_2$ represent hydrogen.

5. The compounds of claim 1, wherein said cycloalkyl or heterocycloalkyl group is selected from 3~8 membered rings.

6. The compounds according to claim 1, wherein $R_1$, $R_2$, and $R_4$ represent hydrogen.

7. The compounds according to claim 1, wherein $R_3$ and $R_5$ represent methyl.

8. The compounds according to claim 1, wherein $R_6$ and $R_7$ represent $R_9O$ and $R_{10}O$, $R_9=R_{10}=H$.

9. The compounds according to claim 1, wherein $R_1$, $R_2$, and $R_4$ represent hydrogen, $R_3$, $R_5$ represent methyl and wherein $R_6$ and $R_7$ represent $R_9O$ and $R_{10}O$ $R_9=R_{10}=H$.

10. A method for preparing a compound of formula II, which comprises the step of reacting a compound of formula I with (meth)acrylonitrile,

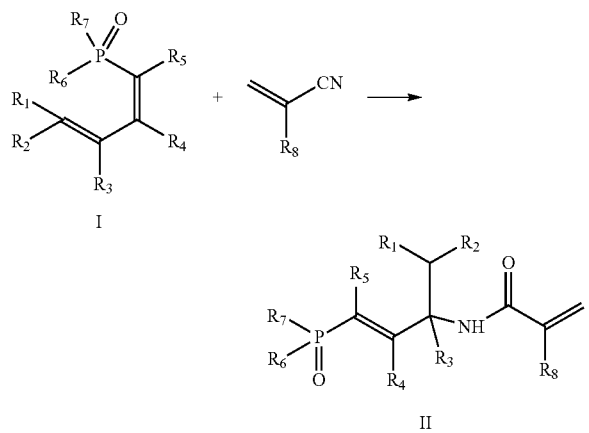

Wherein, $R_1$, $R_2$, $R_3$, $R_4$, $R_5$, $R_6$ and $R_7$ represent, independently, hydrogen, alkyl, aryl, alkaryl, aralkyl, cycloalkyl, heterocycloalkyl, or alkenyl groups;

$R_6$ and $R_7$ represents $R_9O$, and $R_{10}O$ respectively wherein $R_9$ and $R_{10}$ represents hydrogen, alkyl, aryl, alkaryl, aralkyl, cycloalkyl, alkenyl groups, or metals selected from the group consisting of Na, Li, Ca;

$R_8$ represents H, or $CH_3$; and wherein any two of $R_1$, $R_2$, $R_3$, $R_4$ and $R_5$ are together formed into a cycloalkyl, or heterocycloalkyl group.

11. The method of claim 10, wherein the said alkyl, alkenyl comprise from 1~24 carbon atoms, said aryl comprises from 6~24 carbon atoms, said alkaryl, aralkyl comprise from 7~24 carbon atoms, and said cycloalkyl, heterocycloalkyl comprise from 3~24 carbon atoms.

12. The method of claim 10, wherein the said alkyl, alkenyl comprise from 1~18 carbon atoms, said aryl comprises from 6~18 carbon atoms, said alkaryl, aralkyl comprise from 7~18 carbon atoms, and said cycloalkyl, heterocycloalkyl comprise from 3~18 carbon atoms.

13. The method of claim 10, wherein $R_1$ and/or $R_2$ represent hydrogen.

14. The method of claim 10, wherein said cycloalkyl or heterocycloalkyl group is selected from 3~8 membered rings.

15. The method according to claim 10, wherein $R_1$, $R_2$, and $R_4$ represent hydrogen.

16. The method according to claim 10, wherein $R_3$ and $R_5$ represent methyl.

17. The method according to claim 10, wherein $R_6$ and $R_7$ represent $R_9O$ and $R_{10}$, $R_9=R_{10}=H$.

18. The method according to claim 10, wherein $R_1$, $R_2$, and $R_4$ represent hydrogen, $R_3$, $R_5$ represent methyl and wherein $R_6$ and $R_7$ represent $R_9O$ and $R_{10}$, $R_9=R_{10}=H$.

19. The method according to claim 10, wherein said compound I is added in the molar ratio of (0.1~1):1 relative to said (meth)acrylonitrile.

20. The method according to claim 19, wherein said compound I is added in the molar ratio of (0.8~1):1 relative to said (meth)acrylonitrile.

21. The method according to claim 10, wherein the reaction time remains 4~24 hours.

22. The method according to claim 21, wherein the reaction time remains 5~18 hours.

23. The method according to claim 10, wherein the reaction temperature remains 0~100° C.

24. The method according to claim 23, wherein the reaction temperature remains 30~60° C.

25. A polymer or co-polymer of the compounds of formula II according to claim 1.

26. A method for water treatment, rheology modifier applications, surface treatment applications, oilfield applications, mining applications, dental applications, plastics, and/or as flame retardants comprising the step of using compounds of formula II according to claim 1.

27. A method for water treatment, rheology modifier applications, surface treatment applications, oilfield applications, mining applications, dental applications, plastics, and/or as flame retardants comprising the step of using a polymer or co-polymer according to claim 25.

* * * * *